United States Patent
Manz et al.

(10) Patent No.: US 6,540,896 B1
(45) Date of Patent: Apr. 1, 2003

(54) OPEN-FIELD SERIAL TO PARALLEL CONVERTER

(75) Inventors: Andreas Manz, East Molesey (GB); Luc J. Bousse, Los Altos, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/369,050

(22) Filed: Aug. 4, 1999

Related U.S. Application Data

(60) Provisional application No. 60/095,403, filed on Aug. 5, 1998.

(51) Int. Cl.[7] .......................... B01D 57/02; B01D 59/42; B01D 59/50; B01D 61/42; B01D 61/58; B01L 3/02; B01L 3/00; G01N 1/10

(52) U.S. Cl. ....................... 204/451; 204/450; 204/600; 204/601; 422/100; 422/102; 436/180

(58) Field of Search ................................ 204/450, 451, 204/600, 601; 422/70, 100, 99, 102; 436/180

(56) References Cited

U.S. PATENT DOCUMENTS

| | | | |
|---|---|---|---|
| 4,390,403 A | | 6/1983 | Batchelder |
| 4,465,582 A | * | 8/1984 | Richman ................. 204/299 R |
| 4,636,296 A | * | 1/1987 | Kunz ....................... 204/182.5 |
| 4,908,112 A | | 3/1990 | Pace |
| 5,069,768 A | * | 12/1991 | Plaas-Link ............... 204/180.1 |
| 5,126,022 A | | 6/1992 | Soane et al. |
| 5,498,392 A | | 3/1996 | Wilding et al. |
| 5,571,410 A | | 11/1996 | Swedberg et al. |
| 5,585,069 A | | 12/1996 | Zanzucchi et al. |
| 5,593,838 A | | 1/1997 | Zanzucchi et al. |
| 5,599,432 A | | 2/1997 | Manz et al. |
| 5,603,351 A | | 2/1997 | Cherukuri et al. |
| 5,635,358 A | | 6/1997 | Wilding et al. |
| 5,637,469 A | | 6/1997 | Wilding et al. |
| 5,699,157 A | | 12/1997 | Parce |
| 5,750,015 A | | 5/1998 | Soane et al. |
| 5,779,868 A | | 7/1998 | Parce et al. |
| 5,800,690 A | | 9/1998 | Chow et al. |

(List continued on next page.)

FOREIGN PATENT DOCUMENTS

| | | |
|---|---|---|
| WO | WO 9604547 | 2/1996 |
| WO | WO 9702357 | 1/1997 |
| WO | WO 9800231 | 1/1998 |

OTHER PUBLICATIONS

Cohen, C.B. et al., "A Microchip–Based Enzyme Assay for Protein Kinase A," *Anal. Chem.* (1999) 273:89–97.

Dasgupta, P.K. et al., "Electroosmosis: A Reliable Fluid Propulsion System for Flow Injection Analysis," *Anal. Chem.* (1994) 66:1792–1798.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

(List continued on next page.)

*Primary Examiner*—Jill Warden
*Assistant Examiner*—Brian R. Gordon
(74) *Attorney, Agent, or Firm*—Paul Littlepage; Jonathan Alan Quine; Quine Intellectual Property Law Group, P.C.

(57) ABSTRACT

Microfluidic devices and systems for affecting the serial to parallel conversion of materials introduced into the device or system. Material or materials to be converted from a serial orientation, e.g., a single channel, into a parallel orientation, e.g., multiple channels, are introduced into an open chamber or field in which containing flows of materials maintain the cohesiveness of the sample material plugs serially introduced into the open chamber. The sample material or materials are then redirected in the chamber toward and into a plurality of parallel channels that also communicate with the chamber.

20 Claims, 14 Drawing Sheets

U.S. PATENT DOCUMENTS

| | | | | |
|---|---|---|---|---|
| 5,824,204 A | * | 10/1998 | Jerman | 204/601 |
| 5,842,787 A | | 12/1998 | Kopf-Sill et al. | |
| 5,846,396 A | * | 12/1998 | Zanzucchi et al. | 204/601 |
| 5,852,495 A | | 12/1998 | Parce | |
| 5,858,187 A | * | 1/1999 | Ramsey et al. | 204/452 |
| 5,869,004 A | | 2/1999 | Parce et al. | |
| 5,876,675 A | | 3/1999 | Kennedy | |
| 5,880,071 A | | 3/1999 | Parce et al. | |
| 5,882,465 A | | 3/1999 | McReynolds | |
| 5,885,470 A | | 3/1999 | Parce et al. | |
| 5,906,724 A | * | 5/1999 | Sammons et al. | 204/450 |
| 5,928,880 A | * | 7/1999 | Wilding et al. | 435/7.21 |
| 5,942,443 A | | 8/1999 | Parce et al. | |
| 5,948,227 A | | 9/1999 | Dubrow | |
| 5,955,028 A | | 9/1999 | Chow | |
| 5,957,579 A | | 9/1999 | Kopf-Sill et al. | |
| 5,958,203 A | | 9/1999 | Parce et al. | |
| 5,958,694 A | | 9/1999 | Nikiforov | |
| 5,959,291 A | | 9/1999 | Jensen | |
| 5,964,995 A | | 10/1999 | Nikiforov et al. | |
| 5,965,001 A | | 10/1999 | Chow et al. | |
| 5,965,410 A | | 10/1999 | Chow et al. | |
| 5,972,187 A | | 10/1999 | Parce et al. | |
| 5,976,336 A | | 11/1999 | Dubrow et al. | |
| 5,985,119 A | * | 11/1999 | Zanzucchi et al. | 204/450 |
| 5,989,402 A | | 11/1999 | Chow et al. | |
| 6,001,231 A | | 12/1999 | Kopf-Sill | |
| 6,004,515 A | | 12/1999 | Parce et al. | |
| 6,011,252 A | | 1/2000 | Jensen | |
| 6,012,902 A | | 1/2000 | Parce | |
| 6,042,709 A | * | 3/2000 | Parce et al. | 204/453 |
| 6,086,825 A | * | 7/2000 | Sunberg et al. | 422/100 |
| 6,120,666 A | * | 9/2000 | Jacobson et al. | 204/452 |
| 6,132,578 A | * | 10/2000 | Lambara et al. | 204/451 |
| 6,156,273 A | * | 12/2000 | Regnier et al. | 422/70 |
| 6,184,029 B1 | * | 2/2001 | Wilding et al. | 435/287.1 |
| 6,241,866 B1 | * | 6/2001 | Mir | 204/524 |
| 6,254,754 B1 | * | 7/2001 | Ross et al. | 204/548 |
| 6,267,858 B1 | * | 7/2001 | Parce et al. | 204/600 |
| 6,274,089 B1 | * | 8/2001 | Chow et al. | 422/101 |
| 6,284,113 B1 | * | 9/2001 | Bjornson et al. | 204/453 |

OTHER PUBLICATIONS

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

* cited by examiner

Serial

Converter

Parallel

Serial

Parallel

Serial

Converter

Parallel

Serial

Multiple Serial

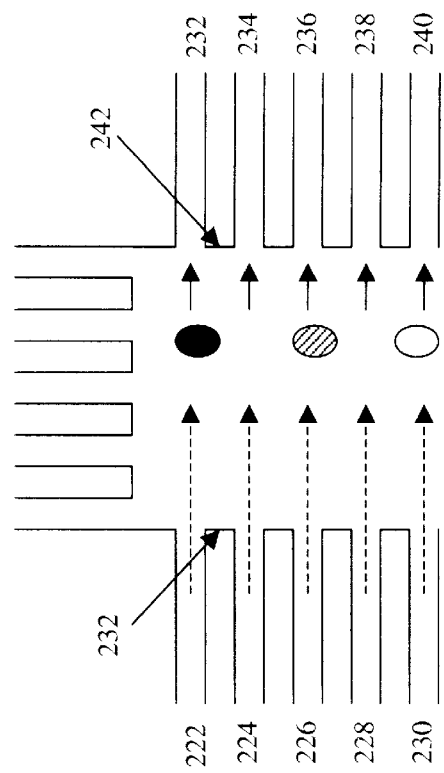
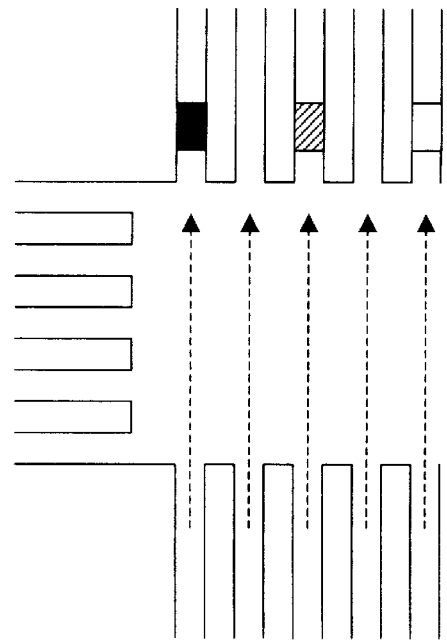
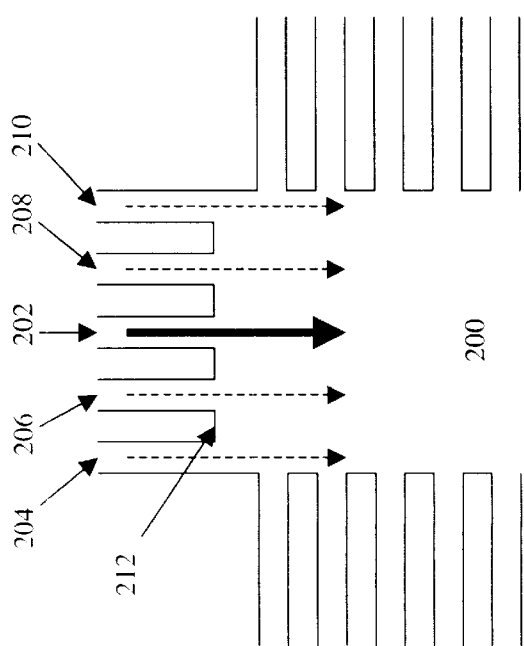
Figure 2A
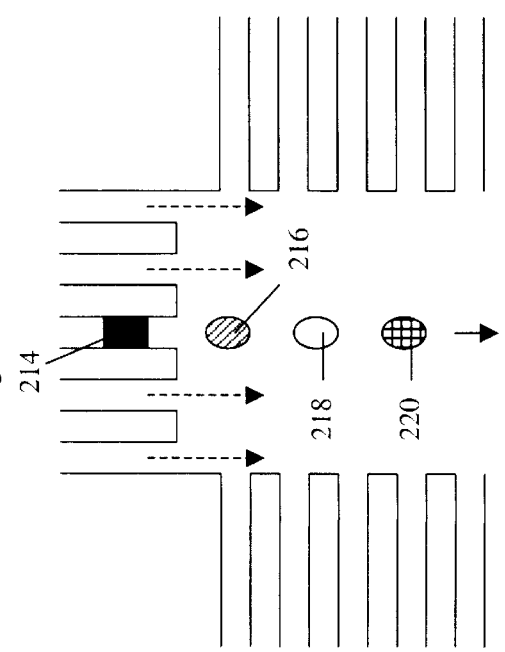
Figure 2B
Figure 2C
Figure 2D

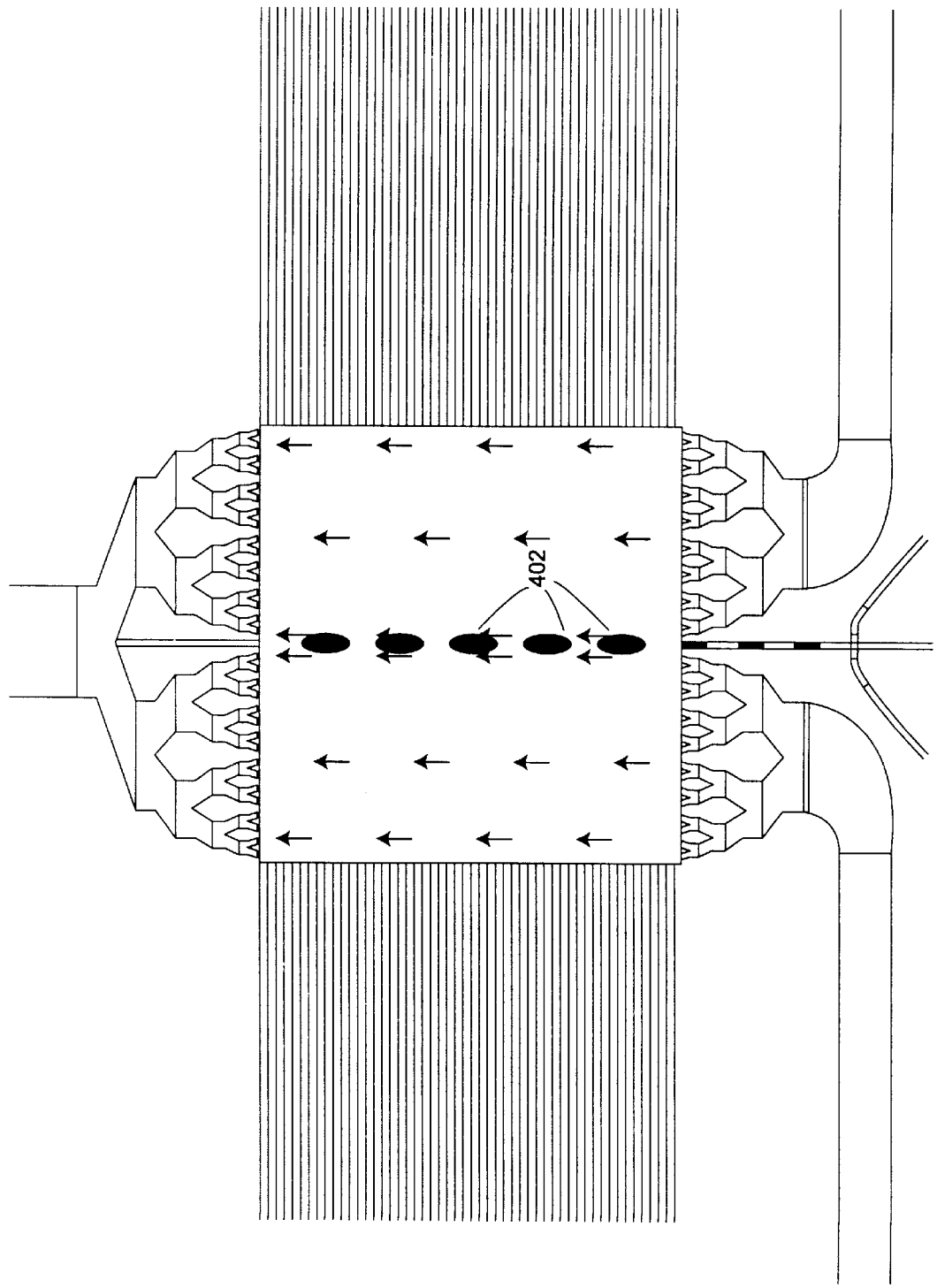

OPEN-FIELD SERIAL TO PARALLEL CONVERTER

CROSS REFERENCE TO RELATED APPLICATIONS

This application claims priority to Provisional Patent Application No. 60/095,403, filed Aug. 5, 1998, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported in part by a grant from the United States National Institute of Standards and Technology (NIST), through the Advanced Technology Program (ATP) under Grant No. 70NANB8H4000.

BACKGROUND OF THE INVENTION

In the electronics industry, manufacturers and developers have sought to increase product performance, speed and capacity, as well as the profits derived therefrom, through miniaturization. Likewise, the pharmaceutical, biotechnology and related industries have sought similar benefits through miniaturization and automation of operations and processes performed in those industries. Performance of more and more operations in less and less space has thus become of primary interest in these industries. Space, therefore, while perhaps not the final frontier, remains an area that invites substantial exploitation.

To achieve this miniaturization the biotechnology and pharmaceutical industries have recently applied some of the same technologies which proved effective in the electronics industry, such as photolithography, wet chemical etching, laser ablation, etc., to the microfabrication of fluidic devices for use in chemical and biological applications. For example, as early as 1979, researchers reported the fabrication of a miniature gas chromatograph on a silicon wafer (discussed in Manz et al., Adv. in Chromatog. (1993) 33:1–66, citing Terry et al., IEEE Trans. Electron. Devices (1979) ED-26:1880). These fabrication technologies have since been applied to the production of more complex devices for a wider variety of applications.

Some examples of microfluidic devices and systems for performing complex reactions, analyses and syntheses are described in, e.g., Published International Application No. WO 98/00231, WO 98/22811, U.S. Pat. Nos. 5,779,868 and 5,858,195, each of which is incorporated herein by reference. Many of the systems developed to date operate by serially introducing samples into a particular analysis channel, wherein the samples are individually analyzed. Higher throughput systems are generally provided by multiplexing the basic system, i.e., incorporating multiple identical analysis channels in parallel, each channel having a separate sample introduction port. In order to further enhance throughput of these systems, systems that are capable of translating serially input compounds into a number of parallel channels for analysis have been developed. These systems are generally termed "serial to parallel converters." Generally, such systems are described in detail in commonly owned Published International Application No. 98/22811, which is incorporated herein by reference.

Despite the development of these systems, it would generally be desirable to provide such systems with enhanced throughput by allowing each analysis unit, e.g., an analysis channel, to be applied to multiple serial analyses of different samples, as well as enhanced control of materials during the serial to parallel conversion process. The present invention meets these and a variety of other needs.

SUMMARY OF THE INVENTION

The present invention generally provides microfluidic devices and systems for affecting the serial to parallel conversion of materials introduced into the device or system. The present invention generally accomplishes this by introducing the material or materials to be converted, into an open chamber or field in which constraining flows of materials maintain the cohesiveness of the sample material plugs serially introduced into the open chamber.

In at least one aspect, the present invention provides microfluidic devices that comprise a body structure having a first chamber disposed therein, where the chamber has at least two sets of opposing sides. Also provided is a first sample introduction channel in fluid communication with the chamber on a first side. A first plurality of parallel channels are provided in fluid communication with the chamber on a second side that is not opposite to the first side and a second plurality of channels in fluid communication with the chamber on a third side, the third side being opposite the second side.

The present invention also provides methods of performing serial to parallel conversion of materials. At least one method comprises providing a body having disposed therein an open field chamber having at least first and second sides opposite one another, a first plurality of channels fluidly connected to the first side of the chamber at periodic intervals, and a second plurality of channels fluidly connected to the second side of the chamber at periodic intervals. A quantity of a sample material is introduced into the chamber between the two sides. Flow of the material is directed from the chamber into a subset of the second plurality of channels by directing flow of a carrier material from each of the first plurality of channels into the chamber.

BRIEF DESCRIPTION OF THE FIGURES

FIGS. 2A–2D schematically illustrate the control of material movement in an open-field in accordance with the present invention.

FIGS. 4A and 4B schematically illustrate serial to parallel conversion within the open field device illustrated in FIG. 3.

DETAILED DESCRIPTION OF THE INVENTION

I. General

Figure 1A:
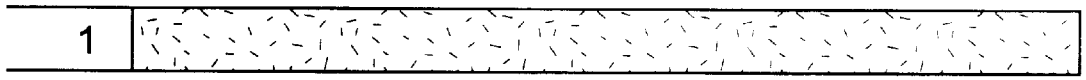
FIGS. 1A–1D schematically illustrate the principles of serial to parallel conversion.
Figure 1A:
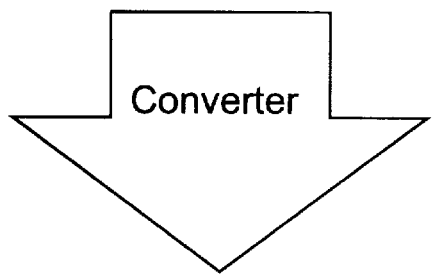
Figure 1A:
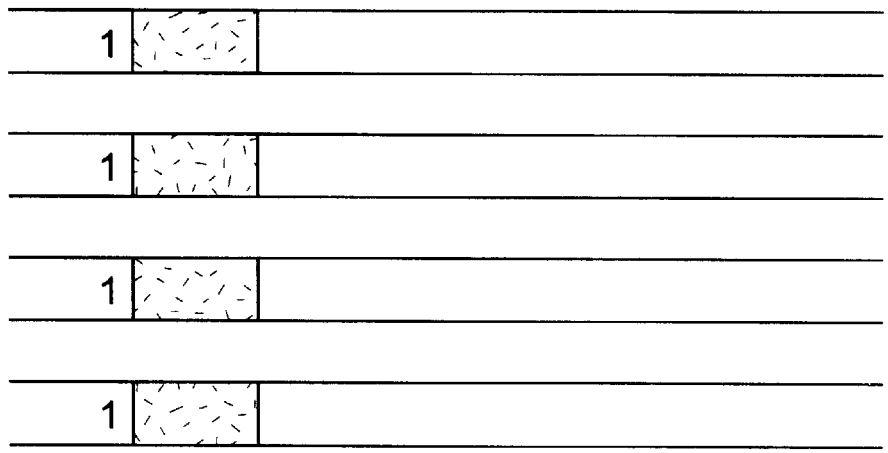
Figure 1B:
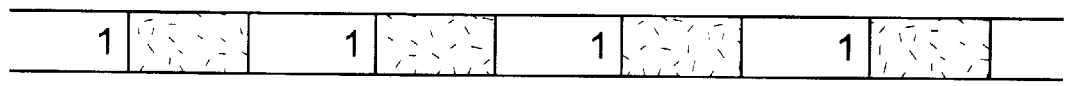
Figure 1B:
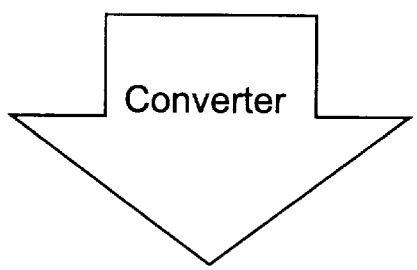
Figure 1B:
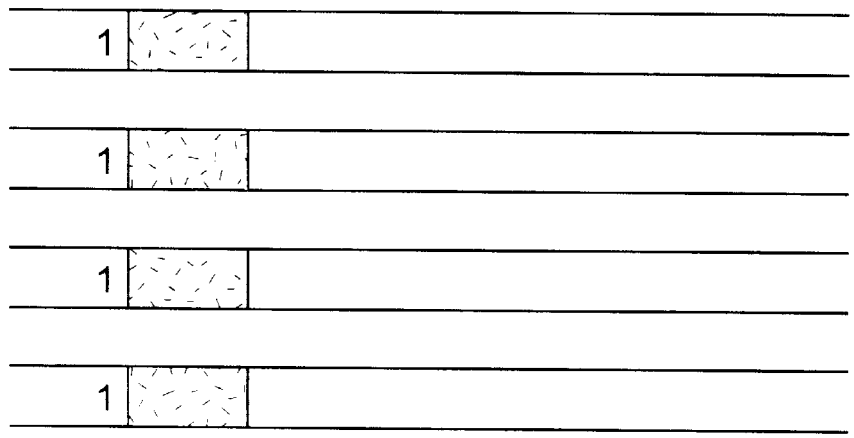
Figure 1C:
Figure 1C:
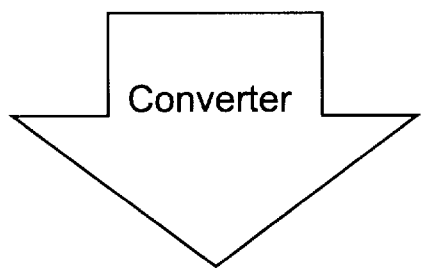
Figure 1C:
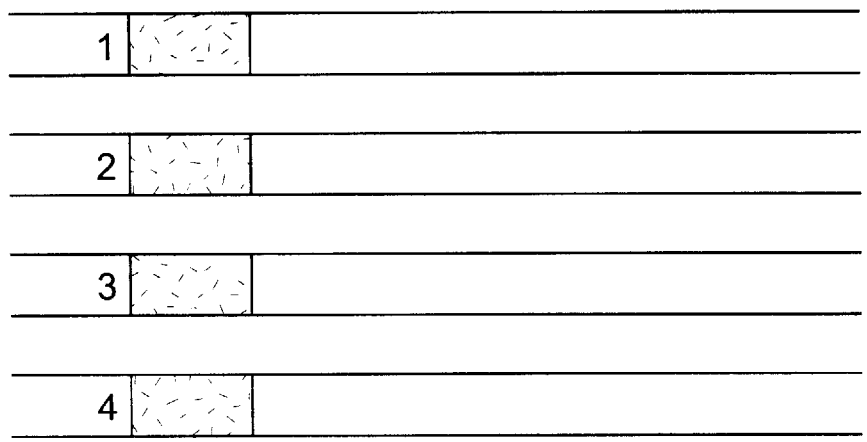
Figure 1D:
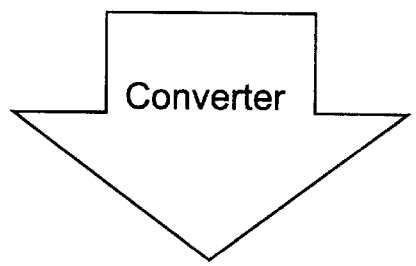

The present invention generally provides microfluidic devices and systems that are capable of performing extremely high-throughput experimentation by virtue of their ability to take up large numbers of different compounds in a serial fashion or orientation, and translate those serially oriented samples into a parallel analysis orientation. As used herein, "serial to parallel conversion" refers to the ability to translate at least two samples introduced into or through a single channel in a serial fashion, e.g., one after another, into two or more parallel channels, such that materials that were serially oriented in a single channel are now oriented in parallel in separate channels. Typically, this has been carried out by introducing the serially oriented materials into a single channel that is intersected by a number of parallel channels. Once the materials are introduced into the first channel, the direction of material or fluid flow within the system is controllably altered to direct materials into and through the various parallel channels. A number of methods and channel geometries are available for controlling flow of material into the parallel channels, see, e.g., WO 98/00231 and WO 98/22811, previously incorporated herein.

FIG. 1 schematically illustrates the principles of serial to parallel conversion. For example, FIG. 1A illustrates the conversion of a single large volume or continuous stream of material, serially input into a microfluidic device, into a plurality of discrete and parallel analysis channels. A similar process is illustrated in FIG. 1B where a plurality of discrete volumes of a particular sample material serially input into the device, are aliquoted into separate parallel channels. Serial to parallel conversion also involves the allocation of a plurality of different materials into separate parallel channels, e.g., as shown in FIG. 1C, as well as the aliquoting of small amounts of the different materials into each of the different parallel channels, e.g., as shown in FIG. 1D.

While the above noted methods, devices and systems are effective at carrying out serial to parallel conversion of materials, the inclusion of large numbers of intersections can sometimes have adverse convective effects on the cohesiveness of discrete material plugs or volumes. Specifically, while methods are available for controlling flow at intersections, this becomes difficult where there are a number of serially oriented intersections, particularly where material in each analysis is desired to be the same. Typically, controlling flow at intersections relies upon the introduction of constraining flows from the channels coming into the main channel, e.g., the side channels. In serially oriented intersections, these constraining materials would dilute out the material of interest that is in the main channel.

In accordance with the present invention therefore, the actual converting event for all of the serially oriented materials is carried out in an open chamber, as opposed to within a single channel intersected by large numbers of parallel channels. By performing the translation of material plugs from serial to parallel orientation in an open area, the dispersive and/or convective effects of the intersections are avoided.

In order to maintain the cohesiveness of the material plugs in the open chamber or field, a number of parallel containing flows are typically applied in the same direction as the direction of flow of the materials being analyzed. Generally, this is accomplished by way of a number of containing flow channels that intersect the chamber such that flow from those channels proceeds across the chamber in a direction parallel to the flow of the sample material, e.g., the channels come into the chamber along one edge. In particular, flowing materials tend to disperse or broaden substantially when entering a larger area, e.g., a chamber, from a smaller area, e.g., a channel. This effect is accentuated in electrokinetically driven materials as a result of the field dispersion in the wider area. This field dispersion is contained by applying matching fields through the containing flow channels, which in turn, contain the materials flowed into the open chamber or field. Similarly, in pressure based flow, dispersion of materials is controlled by forcing matching fluid flows through the containing flow channels. Similar containing flows are optionally or additionally provided: upon the switching of the direction of fluid flow, via the large numbers of feed channels to again control the movement of the sample material in the open chamber. As a result, the only dispersive effects remaining in the open field would be the diffusion effects of the material in the particular medium. A schematic illustration of the open field flow control and serial to parallel conversion methods of the invention is shown in FIGS. 2A–2D.

Briefly, FIG. 2A illustrates an open field or chamber 200. A reagent or sample introduction channel 202 is provided in communication with the chamber 200 such that the reagent or material is introduced into a central portion of the chamber. This is illustrated by the darker arrow. Flow of the sample material in the chamber 200 is contained by virtue of parallel material flow within the chamber, e.g., as illustrated by the dashed arrows. Typically, this parallel containing flow is directed from a number of channels 204–210 that communicate with the chamber in a fashion parallel to the sample or reagent introduction channel 202. As shown, the channels communicate with the chamber 200 at adjacent points along the same side 212 of the rectangular chamber, such that the flow of material from each of the channels 202–210 is parallel.

FIGS. 2B–2D illustrate how these containing flows are used to affect the serial to parallel conversion of material. In particular, as shown in FIG. 2B, a plurality of discrete quantities, plugs or volumes of sample material 214–220 are transported through the reagent introduction channel 202 into the chamber 200. As shown, the sample plugs comprise a number of different types of sample material (as indicated by their different shading), although the methods of the invention are equally applicable to other serial to parallel conversions, e.g., as. shown in FIGS. 1A–1D. Excessive dispersion or diffusion of the discrete sample quantities is prevented by the concurrent flow of material into the chamber from containing flow channels 204–210 (again, as indicated by the dashed arrows). Once the sample quantities are sufficiently within the chamber 200, the direction of flow is switched. For example, as shown in FIG. 2C, flow from the containing channels 204–210 and sample channel 202 are substantially reduced, stopped or even slightly reversed. Flow is then initiated through the chamber 200 in the new desired direction. In the case of serial to parallel conversion, this desired direction is toward a series of parallel channels. As shown in FIG. 2C, the flow of material is orthogonal to the original direction of flow. This is flow is directed through a second series of parallel flow containing channels 222–230 on one side 232 of the chamber, e.g., a side different from, but not opposite the side 212 through which the sample materials were introduced into the chamber. Again, these parallel flows (shown by the dashed arrows) substantially maintain the cohesiveness of the discrete sample quantities 214–218. The discrete sample quantities are then directed into a series of parallel channels 232–240 (also termed analysis channels) that communicate with the chamber on a side 242 that is opposite side 232 and the second set of flow containing channels, for parallel analysis or subsequent treatment. In addition to maintaining the cohesiveness of the sample quantities 216–220, the second set of parallel flows also direct the sample material into the parallel analysis channels at substantially the same rate, thereby ensuring substantially similar treatment and timing for each sample material in each of these channels.

Due to the relatively large number of integrated channels that are preferred for practicing the present invention, e.g., in parallel containing flow channels, etc., and as noted above, it is generally preferred to use integrated microfluidic channel networks or devices in practicing the invention. As used herein, the term "microfluidic" refers to devices, and/or systems having one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device. In preferred aspects, the bottom portion of the device comprises a solid substrate that is substantially planar in structure, and which has at least one substantially flat upper surface. A variety of substrate materials may be employed as the bottom portion. Typically, because he devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. No. 5,885,470, filed Apr. 14, 1997, and which is incorporated herein by reference in its entirety for all purposes. and which is incorporated herein by reference in its entirety for all purposes.

The channels and/or chambers of the microfluidic devices are typically fabricated into the upper surface of the bottom substrate or portion, as microscale grooves or indentations, using the above described microfabrication techniques. The top portion or substrate also comprises a first planar surface, and a second surface opposite the first planar surface. In the microfluidic devices prepared in accordance with the methods described herein, the top portion also includes a plurality of apertures, holes or ports disposed therethrough, e.g., from the first planar surface to the second surface opposite the first planar surface.

Performing serial to parallel conversion within the devices of the invention and according to the methods of the invention, can be carried out using a variety of different material transport mechanisms, e.g., fluid flow systems. For example, pressure based flow systems using either external or integrated pumping mechanisms or pressure sources can drive fluid or material flow in the devices described herein. In preferred aspects, however, the devices and methods of the invention utilize controlled electrokinetic material and/or fluid transport systems to direct the serial to parallel conversion process. Specifically, electrokinetic transport systems are used to serially introduce sample materials into the devices of the present invention, and to translate or 'convert' those serially oriented sample materials into a parallel orientation. The use of electrokinetic material transport systems has been described in detail in, e.g., WO 98/00231, previously incorporated herein by reference.

II. Devices and Systems

Figure 3A:
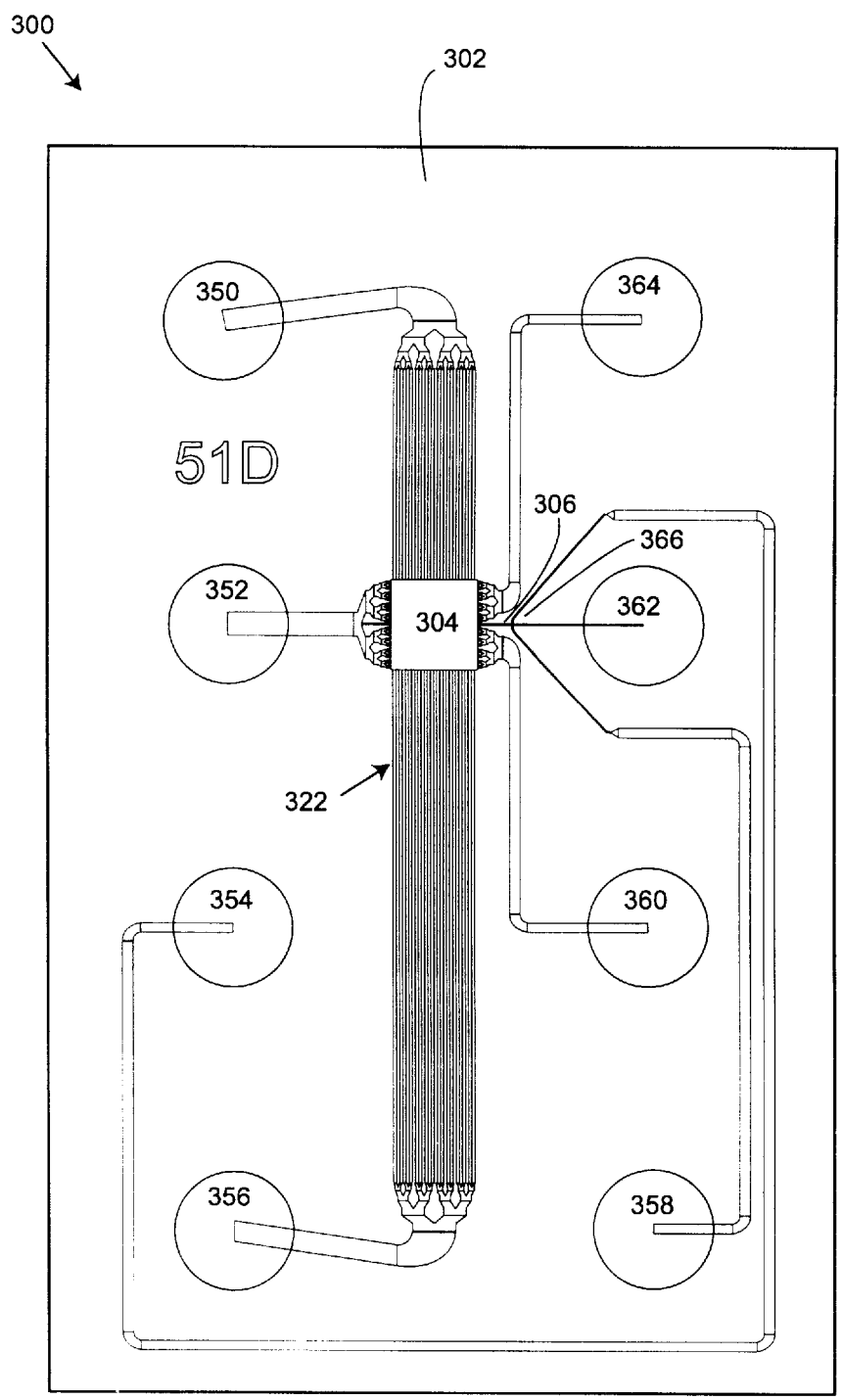
FIGS. 3A and 3B illustrate a microfluidic device for carrying out open-field serial to parallel conversion, according to the present invention.

As noted above, the microfluidic devices of the present invention are typically fabricated into the surface of a planar solid substrate and bonded to a second solid substrate to seal the various channels and chambers of the device. Although generally described in this manner, such construction is not required. In particular, microfluidic devices are optionally fabricated from a number of discrete elements, e.g., conduits and chambers, that are joined together in an integrated structure. FIG. 3 schematically illustrates an exemplary microscale channel network for carrying out open-field serial-to-parallel conversion according to the present invention. In particular, FIG. 3A illustrates a microfluidic device 300 that includes a body structure 302 having disposed therein an open chamber or field 304, in which samples serially introduced into the device, e.g., via sample channel 306, are reorganized into a parallel orientation for flowing through a series of parallel analysis channels 322.

Figure 3B:
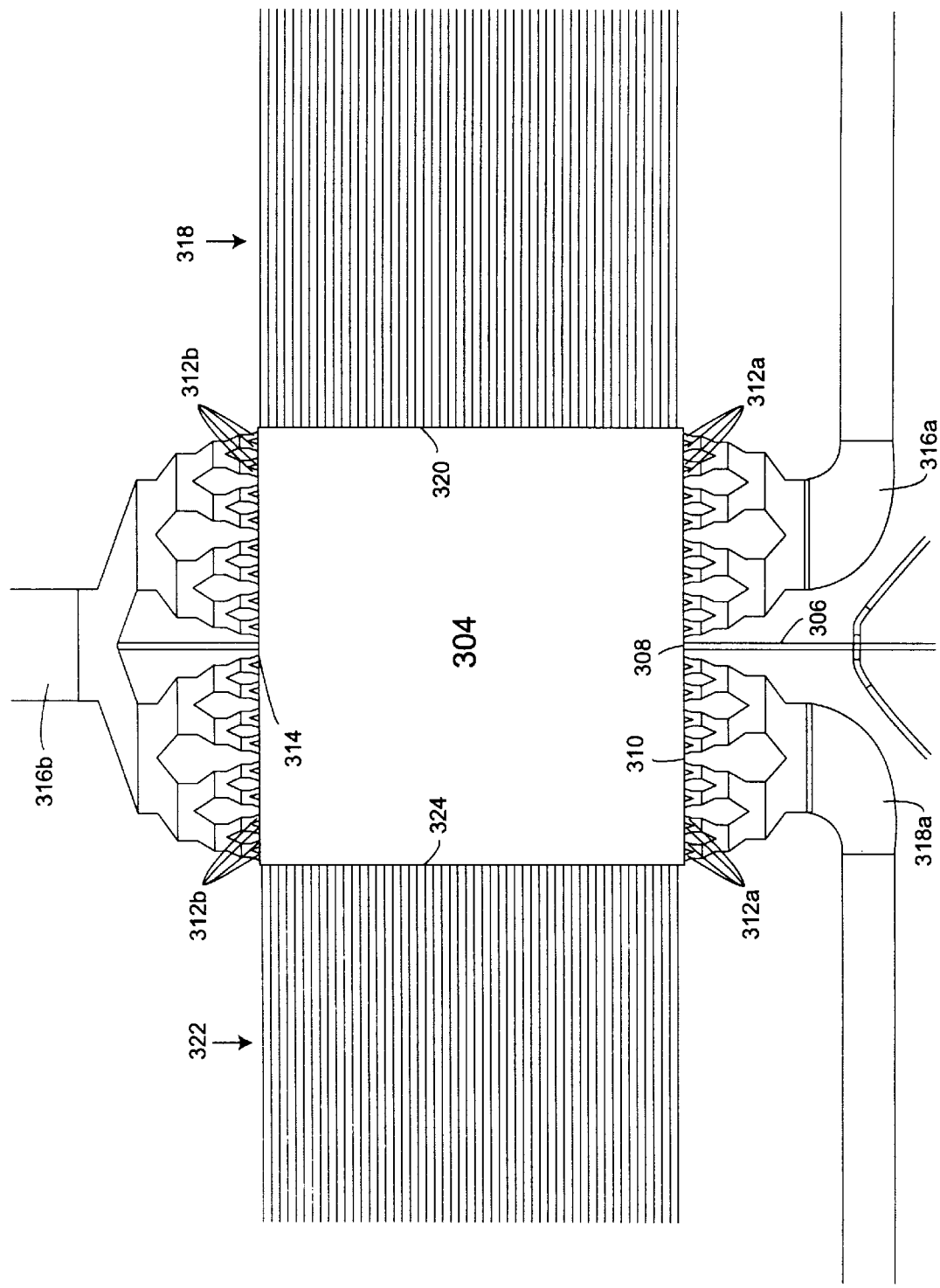

FIG. 3B illustrates an expanded view of the open field 304 and the various channels intersecting the field. The serial sample. introduction channel 306, also disposed in the body structure, is in fluid communication with the open field 304 at an intermediate point 308 along a first side 310 of the field 304. The positioning of the sample introduction channel may be varied depending upon a number of factors. For example, in instances where it is desired to minimize any dispersive effects on samples serially introduced into the open field prior to their transfer to the parallel channels, the introduction channel may be positioned at a point substantially closer to those parallel channels. As a result, there is less time for the samples to diffuse prior to being introduced into the parallel channels.

Containing flow channels 312a are also in fluid communication with the field along the first side 310, on both sides of the sample channel 306. A corresponding series of containing flow channels 312b are also provided on a second side 314 of the field opposite the first side 310. While each the containing flow channels 312a and 312b may be completely distinct channels, as shown, each of the containing flow channels 312a and 312b, is an ultimate bifurcation from individual containing flow channels 316a and 318a, and 316b, respectively.

Typically, at least two additional groups of channels also communicate with the open field 304. These include a series of parallel feed channels 318, which communicate with the field on a third side 320 of the field. A series of parallel analysis channels 322, typically corresponding in number and spacing with the parallel feed channels 318, e.g., the feed channels are co-linear with the analysis channels, communicate with the open field 304 on a fourth side 324 of the field, opposite to the third side 320. Typically, a large number of parallel feed channels and analysis channels are provided in order to prevent perturbing effects associated with materials flowing into channels that are spaced further apart, e.g., from lateral flow. In general, at least 10 parallel feed channels and/or analysis channels are provided per centimeter at the point where they communicate with the open field 304, preferably, at least 20 parallel channels/cm, more preferably, at least 50 channels/cm, and still more preferably, at least 100 parallel channels/cm. In addition to prevent adverse lateral flow effects from having analysis channels spaced further apart, the inclusion of more analysis channels ensures the greatest likelihood of maintaining separation between adjacent samples, e.g., post serial to parallel conversion, and having some channels with maximum potential sample concentrations.

Figure 4B:
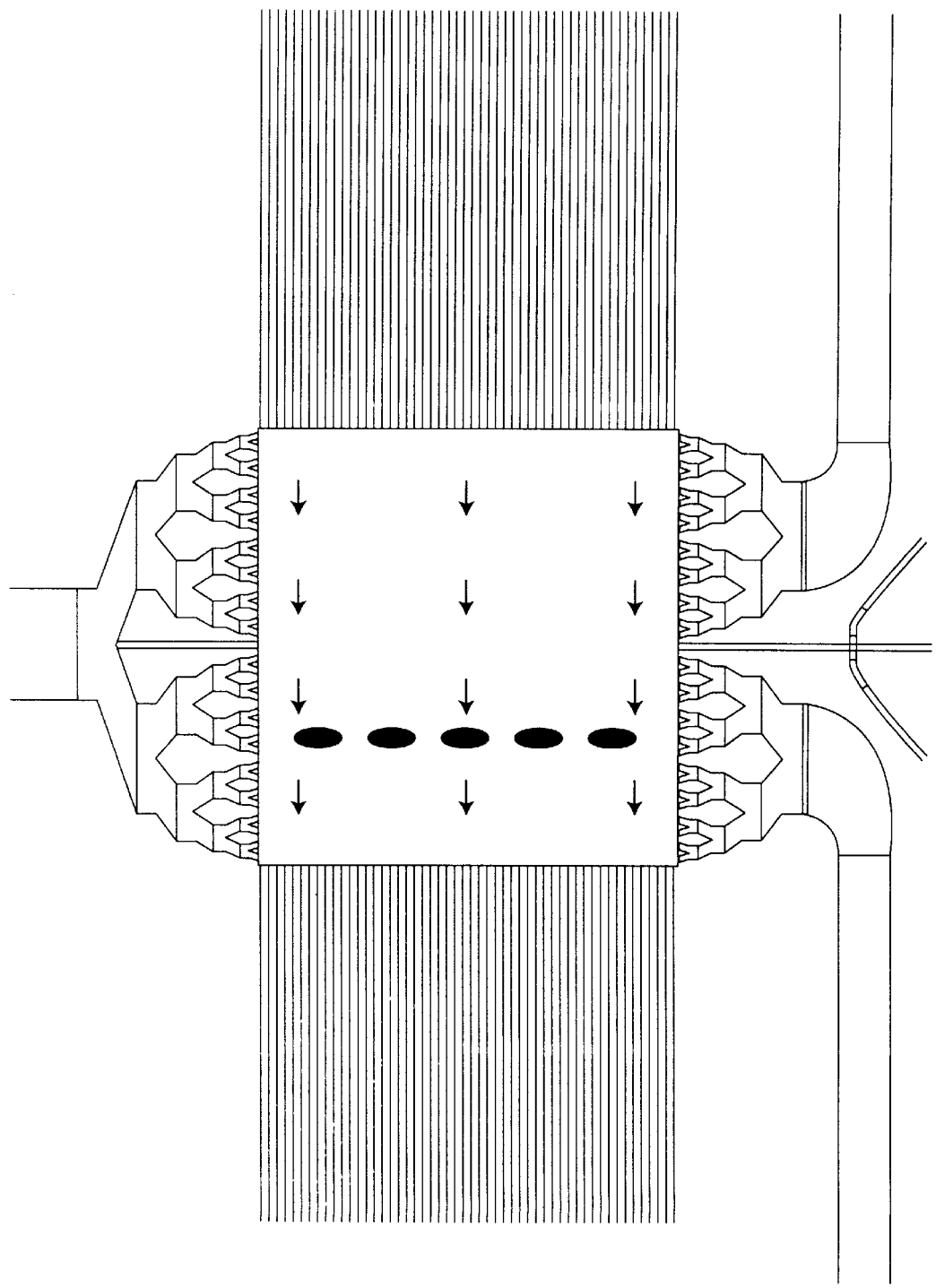

The operation of the open field system is illustrated in FIGS. 4A–C and with reference to FIGS. 3A and 3B. In particular, a volume of sample material 402, or a plurality of discrete volumes of sample material are electrokinetically introduced into the open field 304 via sample introduction channel 306. Typically, the sample introduction channel 306 is in fluid communication with a plurality of sample sources, or is configured to be able to access a plurality of different sample sources. In preferred aspects, the sample introduction channel is in communication with an external sampling capillary element, e.g., an electropipettor (see, U.S. Pat. No. 5,779,868, which is incorporated herein by reference in its entirety for all purposes). The sample or samples are flowed into the open field and transported across the field. Containing flows of material, e.g., buffer, are electrokinetically directed into the open field from channels 312a to channels 312b, as shown by the arrows. These containing flows serve to maintain the cohesiveness of the sample plugs by providing a flowing fluid or ion barrier to constrain the mobility of the sample plugs in the direction lateral to the direction of flow. In particular, in electrokinetic flow systems, field effects can substantially broaden material plugs when they enter larger spaces. The containing flows, however, counteract these field effects, and thereby contain the material plugs within substantially their original spacing. As a result, the only dispersive effects on the material plugs result from the diffusion of the sample material within the open field. Further, even such diffusion effects can be reduced through the incorporation of an appropriate matrix within the open field, e.g., a viscous polymer matrix, or the like. See, e.g., 720 in FIG. 7. As a result, a parade of discrete sample plugs is introduced into the open field.

Once the sample plugs have been transported into the open field, the electrokinetic flow direction is switched such that the sample plugs are transported toward parallel analysis channels 322, e.g., by providing a voltage gradient between feed channels 318 and analysis channels 322. Again, the multiple parallel channels and flow profiles through the open field serve to maintain the cohesiveness of the material plugs. This is illustrated in FIG. 4B, where the new flow direction is illustrated by the arrows. Each of the sample plugs then enters either one or a group of the analysis channels, wherein analysis can occur. Typically, analysis may include, e.g., separation, i.e., of nucleic acid samples, protein samples, or the like. Alternatively, the analysis channels may include interacting components of a biochemical system against which the sample materials are to be screened for effects on that system (see, e.g., WO 98/00231). Once the sample plugs enter the one or group of analysis channels, the ability for the sample plugs to diffuse together is eliminated, because they are constrained by actual physical barriers, thereby immobilizing the sample plugs in one dimension.

A detection zone is provided in the analysis channels 322, at which point the results of the analysis carried out in the analysis channels may be detected. Typically, the analysis will yield an optical signal. As such, the detection zone typically includes a transparent or translucent region of the channels, through which an optically detectable signal may be detected. A detector is generally disposed adjacent to the detection zone so as to receive and record the optically detectable signal.

Introduction of large numbers of discrete sample quantities into the sample or reagent introduction channel for subsequent translation to parallel analysis channels, e.g., as described above, is optionally carried out using an integrated pipettor element that is fluidly connected to the sample introduction channel. One example of such a pipettor element is shown in U.S. Pat. No. 5,779,868, which is incorporated herein by reference, which draws material into a capillary element attached to a microfluidic device, and subsequently moves the sampled material into the sample introduction channel.

In some embodiments, the microfluidic system for converting a serial flow of materials into a parallel flow of materials comprises, e.g., a body structure with a first chamber having at least 2 opposing sides; a first sample introduction channel (in fluid communication with the chamber on a first side ) for transmitting a serial flow of materials; a first plurality of parallel channels (in fluid communication with the chamber on a second side that is not opposite to the first side); a second plurality of parallel channels (in fluid communication with the chamber on a third side, the third side being opposite the second side) for receiving the parallel flow of materials; a controller operably coupled to the first sample introduction channel and to at least one of the first and second plurality of parallel channels, configured to transport the serial flow of materials into the chamber from the first sample introduction channel and to transport the serial flow of materials out of the chamber through the second plurality of parallel channels, thus, the serial flow of materials will be transported into the second plurality of parallel channels in a parallel orientation; and, a detector system operably coupled to one or more channel, wherein the detector system is configured to detect one or more signal from the one or more channel. In yet further embodiments, the system comprises a controller operably coupled to the system, for flowing a sample material from the sample introduction channel into the chamber and for directing a flow of a carrier material through the first plurality of channels into the chamber and from the chamber into the second plurality of channels. In some embodiments, the controller comprises an electrokinetic controller (which optionally comprises an electrical power source (see, e.g., 714 in FIG. 7) and a plurality of electrodes operably coupled to the sample introduction channel as well as the first plurality of channels and the second plurality of channels and wherein the plurality of electrodes optionally is separately coupled to the electrical power supply). However, in other embodiments the controller comprises a pressure-based controller comprising, e.g., at least one pressure or vacuum source operably coupled to at least one of the sample introduction channel, the first plurality of channels and/or the second plurality of channels.

III. Applications

As noted above, serial to parallel conversion is broadly applicable to high throughput analyses. Particularly useful applications include high throughput screening of potential pharmaceutical candidates. Such high throughput screening methods are described in detail in Published International Patent Application No. 98/00231, previously incorporated herein. The devices and methods are readily applied to the high throughput methods etc. described therein.

Additionally, the methods and systems of the invention are also applicable to high throughput analytical applications, e.g., genomics. Specifically, the use of microfluidic devices in analysis of genetic material, e.g., nucleic acids is described in, e.g., Published International Application No. 98/49548, which is incorporated herein by reference. In particular, a number of discrete quantities of sample material, e.g., genetic material, protein, etc. is introduced into the open field, transported into a series of parallel separation channels, separated and analyzed. In these cases, it may be desirable to provide a separation matrix only within the analysis channels, e.g., to prevent premature separation and commingling of the different sample materials. See, e.g., 720 in FIG. 7. This is readily accomplished by either coating the analysis channels with an appropriate polymer/surface coating during fabrication, or by introducing an appropriate matrix into the completed devices. Briefly, when introduced into a terminal port of the analysis channels, the polymer will wick via capillary action, up to the point at which the channel communicates with the chamber, at which point the larger cross section of the chamber will not provide sufficient capillarity to counteract that of the analysis channel, thus confining the separation matrix to the analysis channel.

In still a further application, the conversion effect is used as a selection step. In particular, a contained flow of discrete materials is introduced into the chamber. Based upon a previously identified trait, e.g., detected within the sample introduction channel, particular sample materials are directed into a different one of the parallel analysis channels, e.g., by controlling the converting flow within the chamber to go into a selected analysis channel. An example of such an application is fluorescence activated cell sorting (FACS), where cells or other particles are monitored for the presence of a given trait that yields a fluorescent signal, e.g., enzyme activity, expression of a particular receptor, etc. Once the trait is detected, the cell is flowed through the chamber in a controlled fashion via the first containing flows, see, e.g., FIG. 2B. The cell or other particle is then directed into one of the parallel analysis channels via an appropriately directed flow across the chamber into the desired channel.

Figure 7:
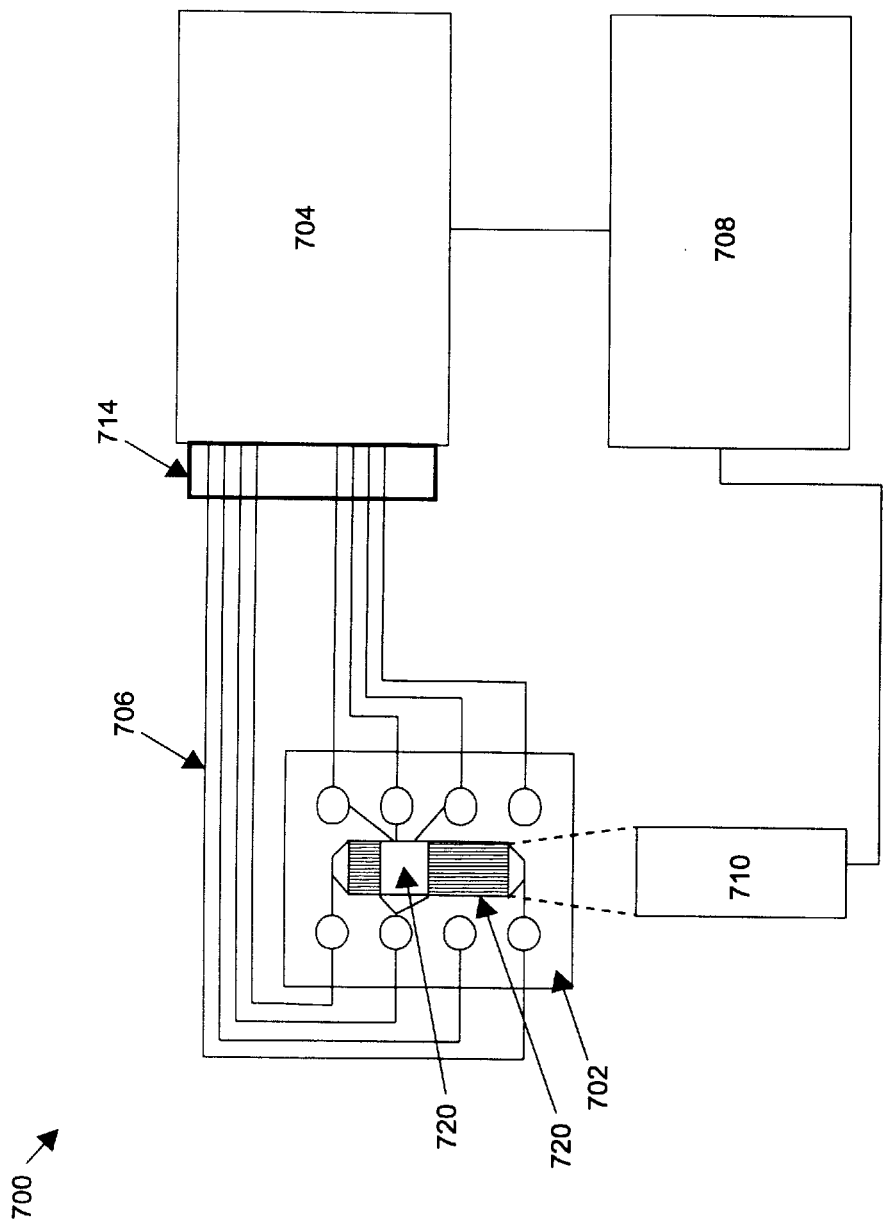
FIG. 7 schematically illustrates an overall system incorporating a microfluidic device as described herein.

Typically, the apparatuses of the invention are combined with other instruments and the like as an integrated system to control and monitor the methods being carried out in such devices. A schematic example of such a system is illustrated in FIG. 7. Briefly, the overall system 700 includes a microfluidic device 702 that includes the open field or chamber as described herein. Control of flows within the device is dictated by the flow controller 704 that is operably coupled to the device, e.g., via connections 706. The nature of the flow controller depends upon the type of motive force that is used to control flow. For example, as shown the flow controller comprises an electrical controller that applies controlled currents through the fluid passages on the device, via electrical connectors 706, to direct fluid or other material movement through electrokinetic forces. Alternatively, the flow controller is a pressure or vacuum source which delivers controlled pressure or vacuum to one or more ports on the device 702, to drive fluid through the channels of the device in a controlled manner. The flow controller 704 is operably coupled to computer 708 which instructs the operation of the controller in accordance with preprogrammed instructions, e.g., to direct flow in the manner desired by the user. Also coupled to computer 708 is detector 710. The detector 710 is also positioned to be in sensory communication with the relevant portions of device 702, e.g., the analysis channels. As used herein, the phrase "in sensory communication" refers to a detector that is positioned and directed so as to be capable of receiving a signal from the channels of the device. Typically, such signals comprise optical signals, requiring the detector to be an optical detector positioned to receive and detect optical signals from the channels of the device which channels typically include at least one transparent wall. However, detectors may optionally or additionally include chemical sensors which, to be in sensory communication may be placed in the channel itself, as well as a variety of other sensor types, e.g., electrical, thermal, radioactivity, and the like. In preferred aspects, the sensor is an optical sensor or sensor array, and preferably, a fluorescence detector, that is capable of detecting signals from all of the analysis channels simultaneously or substantially contemporaneously. Examples of such detectors include, e.g., galvo-scanners, CCD arrays, which are capable of imaging or otherwise detecting optical signals from multiple parallel channels, simultaneously. Signals detected by the detector are then transmitted to the computer for storage and/or analysis

IV. Examples

Figure 5A:
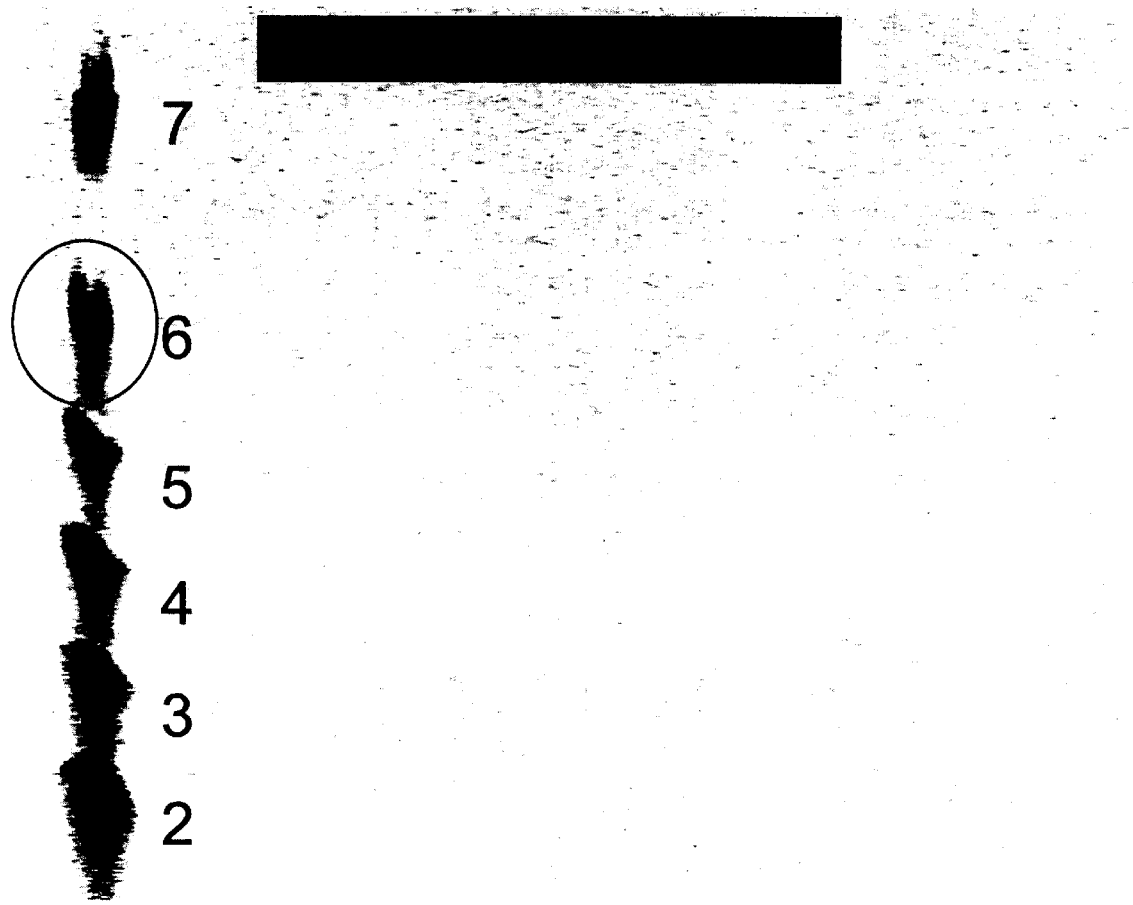
FIGS. 5A and 5B are schematic illustrations showing sample material plugs undergoing serial to parallel conversion in accordance with the present invention.
Figure 5B:
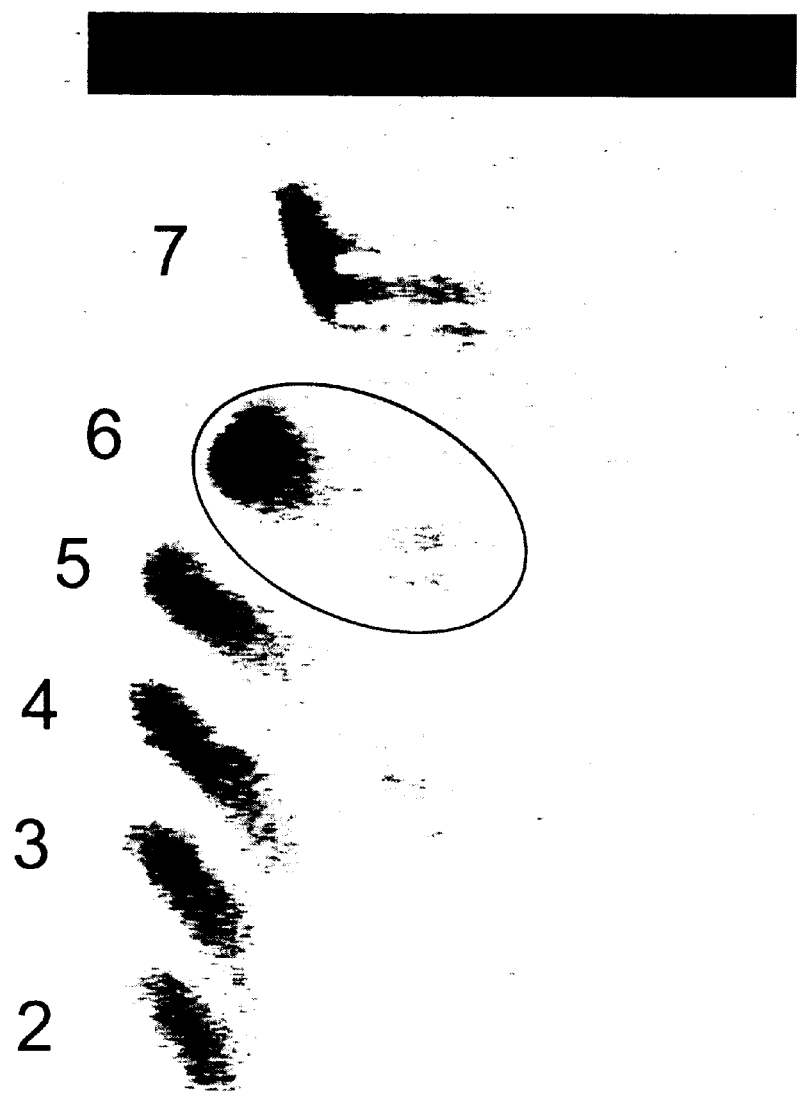

The following examples demonstrate the efficacy of the devices and systems of the present invention. In particular, a microfluidic device having a channel geometry shown in FIG. 3A was used. A representative sample material (Rhodamine B fluorescent dye) was placed in reservoir 358, while buffer was placed into reservoirs 350–356 and 360–364. Plugs of dye were periodically injected into the open field using a standard pinched injection protocol at the sample injection intersection 366. FIG. 5A illustrates a number of discrete dye plugs that were introduced into the open field region in a serial orientation, with appropriate containing flows. FIG. 5B illustrates the same material plugs translated and flowing in a parallel orientation through the open field region and into a series of parallel channels.

Figure 6A:
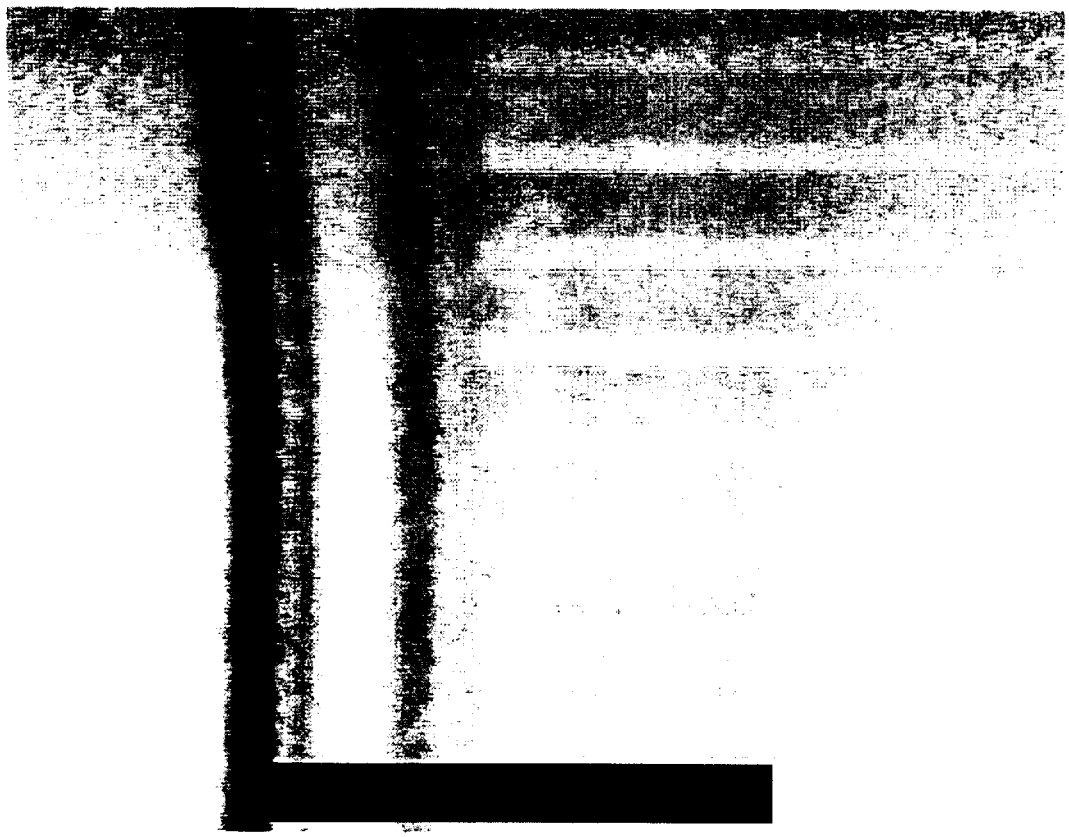
FIGS. 6A and 6B are photographs showing serial to parallel conversion of a stream of sample material, in accordance with the present invention.
Figure 6B:
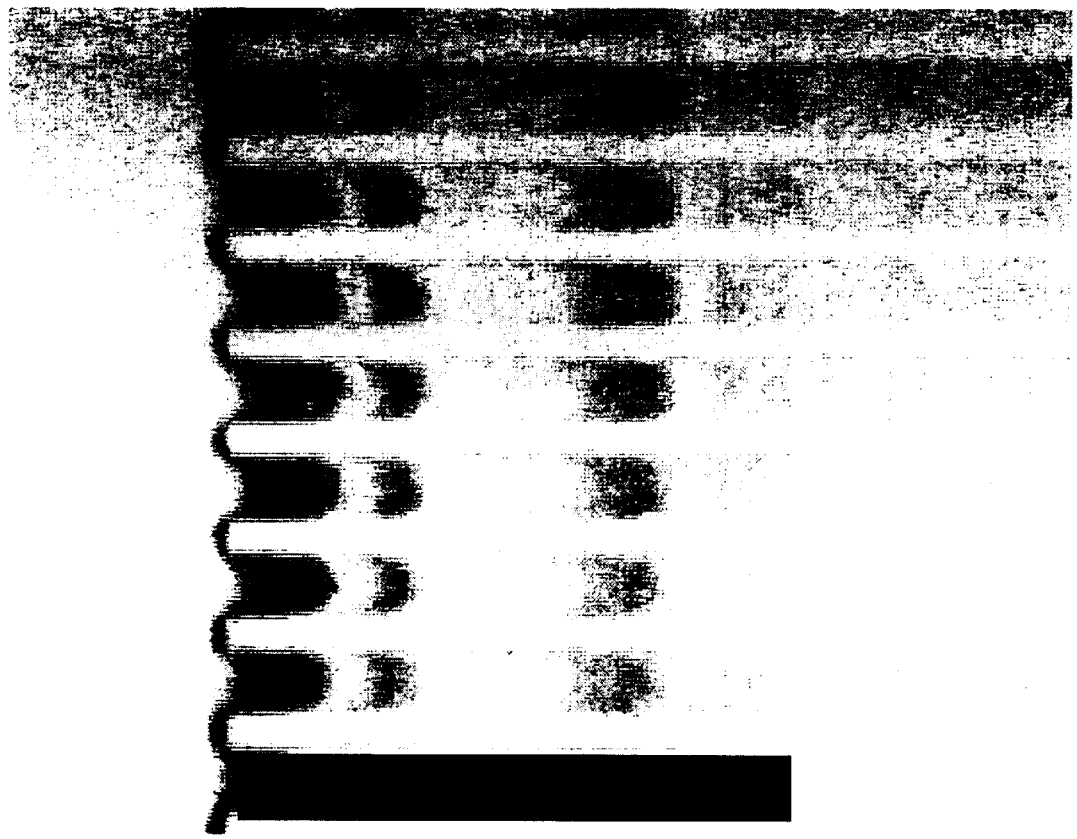

FIG. 6A is a photograph showing the introduction of a stream of a sample of different sized nucleic acid fragments ((ΦX174 cleaved with HaeIII) transported into the open field, followed by a change in flow direction to move the stream toward the parallel channels. FIG. 6B shows the initial separation of the nucleic acid fragments once they enter the numerous parallel channels.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, such illustration is not intended to be limiting. For example, it will be apparent that certain changes and modifications may be practiced within the scope of the appended claims.

We claim:

1. A microfluidic system for converting a serial flow of materials into a parallel flow of materials, the system comprising: a body structure;
   a first chamber disposed within the body structure, the chamber having at least two sets of opposing sides;
   a first sample introduction channel for transmitting the serial flow of materials, in fluid communication with the chamber on a first side;
   a first plurality of parallel channels in fluid communication with the chamber on a second side that is not opposite to the first side;
   a second plurality of parallel channels for receiving the parallel flow of materials, in fluid communication with the chamber on a third side, the third side being opposite the second side;
   a controller operably coupled to the first sample introduction channel and to at least one of the first and second plurality of parallel channels, wherein the controller is configured to transport the serial flow of materials into the chamber from the first sample introduction channel and to transport the serial flow of materials out of the chamber through the second plurality of parallel channels, whereby the serial flow of materials is transported into the second plurality of parallel channels in a parallel orientation; and,
   a detector system operably coupled to one or more channels, wherein the detector system is configured to detect one or more signals from the one or more channels.

2. The microfluidic system of claim 1, wherein the chamber is rectangular.

3. The microfluidic system of claim 1, wherein the chamber and channels have substantially the same depth.

4. The microfluidic system of claim 1, wherein the chamber is between about 1 μm and about 200 μm deep, and has a length or width from about 200 μm to about 1 cm.

5. The microfluidic system of claim 1, wherein the first plurality of channels comprises at least 5 channels in fluid communication with the chamber along the second side.

6. The microfluidic system of claim 1, wherein the second plurality of channels comprises at least 5 channels in fluid communication with the chamber on the third side.

7. The microfluidic system of claim 1, wherein the first plurality of channels comprises at least 10 channels in fluid communication with the chamber along the second side.

8. The microfluidic system of claim 1, wherein the second plurality of channels comprises at least 10 channels in fluid communication with the chamber on the third side.

9. The microfluidic system of claim 1, wherein the first plurality of channels comprises at least 20 channels in fluid communication with the chamber along the second side.

10. The microfluidic system of claim 1, wherein the second plurality of channels comprises at least 20 channels in fluid communication with the chamber on the third side.

11. The microfluidic system of claim 1, wherein the first and second plurality of channels are in fluid communication with the second and third sides of the chamber, whereby each of the second plurality of channels is directly opposite a corresponding channel in the first plurality of channels.

12. The microfluidic system of claim 1, wherein the first plurality of channels is fluidly connected at one end to a common port and at an opposite end to the chamber.

13. The microfluidic system of claim 12, wherein at least one of the fluidic resistance and the electrical resistance of each of the first plurality of channels between the common port and the chamber is substantially equal to the fluidic resistance or electrical resistance of each other of the first plurality of channels between the common port and the chamber.

14. The microfluidic system of claim 1, wherein the second plurality of channels is fluidly connected at one end to a common port and at an opposite end to the chamber.

15. The microfluidic system of claim 14, wherein at least one of the fluidic resistance and the electrical resistance of each of the second plurality of channels between the common port and the chamber is substantially equal to the fluidic resistance or electrical resistance of each other of the second plurality of channels between the common port and the chamber.

16. The microfluidic system of claim 1, wherein the controller comprises an electrokinetic controller.

17. The microfluidic system of claim 16, wherein the electrokinetic controller comprises:
   an electrical power source; and
   a plurality of electrodes operably coupled to the sample introduction channel the first plurality of channels and the second plurality of channels, the plurality of electrodes being separately coupled to the electrical power supply.

18. The microfluidic system of claim 1, wherein the controller comprises a pressure-based controller.

19. The microfluidic system of claim 18, wherein the pressure-based controller comprises at least one pressure or vacuum source operably coupled to at least one of the sample introduction channel, the first plurality of channels and the second plurality of channels.

20. The microfluidic system of claim 1, further comprising a separation matrix disposed in at least the second plurality of channels.

* * * * *